United States Patent [19]

Nilsson et al.

[11] Patent Number: 5,719,048
[45] Date of Patent: Feb. 17, 1998

[54] SEPARATION OF PROTEINS

[75] Inventors: Birgitte Mahler Nilsson, Farum; Mads Aage Laustsen, Lyngby; Christine Pahle, Bagsværd, all of Denmark

[73] Assignee: Novo Nordisk A/S, Bagsvaerd, Denmark

[21] Appl. No.: 513,926

[22] PCT Filed: Mar. 29, 1994

[86] PCT No.: PCT/DK94/00132

§ 371 Date: Sep. 7, 1995

§ 102(e) Date: Sep. 7, 1995

[87] PCT Pub. No.: WO94/22903

PCT Pub. Date: Oct. 13, 1994

[30] Foreign Application Priority Data

Apr. 2, 1993 [DK] Denmark .................................. 396/93

[51] Int. Cl.⁶ .................. C12N 9/00; C12N 9/20

[52] U.S. Cl. .................. 435/183; 435/198; 435/814; 435/816

[58] Field of Search .................. 435/183, 198, 435/814, 816

[56] References Cited

U.S. PATENT DOCUMENTS 3,642,582  2/1972  McClary .................................. 435/183

FOREIGN PATENT DOCUMENTS 0193046  10/1991  European Pat. Off. .

*Primary Examiner*—Leon B. Lankford, Jr.
*Attorney, Agent, or Firm*—Steve T. Zelson, Esq.; Valeta Gregg, Esq.

[57] ABSTRACT

The present invention relates to a method of separating an enzyme from an aqueous solution comprising this enzyme in mixture with other proteins, and recovery of the desired enzyme on crystalline form.

13 Claims, No Drawings

SEPARATION OF PROTEINS

CROSS-REFERENCE TO RELATED APPLICATIONS

This application is a 371 of PCT/DK94/00132 filed Mar. 29, 1994, which is incorporated herein by reference.

TECHNICAL FIELD

The present invention relates to a method of separating an enzyme from an aqueous solution comprising this enzyme in mixture with other proteins, and recovery of the desired enzyme on crystalline form.

BACKGROUND ART

Enzymes are usually provided as liquids or amorphous materials for industrial purposes. When not provided as liquids, they are usually provided as amorphous materials, because the known methods for crystallization of enzymes are usually regarded as too expensive to be used in an industrial scale. This is due to the assumption that crystals can only be grown from very pure and concentrated solutions. In fact, capability of forming crystals is by protein chemists often regarded as evidence of high purity of a protein solution.

Due to the high purity of enzyme crystals, the provision of a cheap and simple method for crystallization of enzymes, which is easily adaptable to an industrial scale, is clearly a desideratum in the industry.

There is an abundance of literature concerning crystallization of enzymes. Characteristic features of the hitherto known crystallization processes are relatively pure and concentrated initial solutions, low yield, very long crystallization time, high consumption of chemicals including organic solvents, and poor industrial adaptability.

The use of low conductivity and pH around pI is in itself far from a new method for crystallization of proteins. It is a technique well described in the literature and is often used for preparation of single crystals for X-ray diffraction from highly purified protein solutions. A. McPherson describes in his book "Preparation and Analysis of Protein Crystals" (Wiley, New York, 1982) how this technique, also known as "salting in" can be used in crystallization. Since then several others have used this method, but only for crystallization from purified solutions. In fact, it is often reported that impurities, and especially other proteins, are regarded as highly undesirable (for reference see A. McPherson in *Eur. J. Biochem.* 289, 1990, pp. 1–23). Thus, the technique in itself is not new, but nobody has ever used it as a purification technique for purification of enzymes in mixtures with other proteins. As such the surprisingly good adaptability on very impure solutions is what makes this technique economically feasible, in that it does not require prepurification by e.g. chromatographic methods.

It is important to distinguish between crystallization and precipitation, the latter resulting in the less pure amorphous form.

In EP patent 193,046 a method for the recovery of an enzyme from a solution thereof is disclosed. By this method the enzyme containing solution is concentrated to supersaturation at a pH value in a range near the isoelectric point of the enzyme, and crystallization is induced. The presence of a salt or organic solvents has been thought essential to any crystallization method. In the above captioned EP 193,046 it is stated that the introduction of salts or organic solvents is unnecessary for the method described, but from the experiments described it is also evident that the enzymes investigated in this patent publication crystallize best in the presence of high salt concentrations, i.e. when the ultrafiltration is followed by vacuum evaporation. Moreover, the method is adapted only to amylases, long crystallization times are required, and the method leads to undesirable amorphous and micro crystalline precipitations.

SUMMARY OF THE INVENTION

It is an object of the present invention to provide a process for the recovery of crystalline enzymes, which process does not require the addition of salts or organic solvents, which permits short crystallization times and high yields, and which is simple and cheap, and compatible to industrial requirements.

Accordingly, the present invention provides a method of separating an enzyme from an aqueous solution comprising the enzyme in mixture with other proteins, which method comprises leaching out salts from the solution, followed by adjustment of the pH of the solution to a level around pI of the enzyme, and subsequent recovery of the enzyme on crystalline form.

DETAILED DISCLOSURE OF THE INVENTION

Hitherto concentrated protein solutions were thought essential to protein crystal production. However, it has now been found that saturation and supersaturation should be avoided during process stages prior to the crystallization stage, since saturation, and in particular supersaturation, during uncontrolled conditions favours the formation of the less desirable amorphous form of the protein by precipitation.

It has now surprisingly been found that by employing the method of invention enzymes become separated from their mixtures with other proteins, even mixtures comprising other enzymes, and the desired enzyme precipitates on crystalline form.

Accordingly, the present invention provides a method for separating enzymes from an aqueous mixture comprising other proteins with different crystallization properties. The method comprises leaching out salts and other low molecular weight impurities from the solution, thereby obtaining a low ionic strength in the solution, followed by adjustment of pH to a level around pI of the desired protein. This method causes the enzyme to precipitate on crystalline form.

The method of invention may be applied to separation/crystallization of any enzyme. In a preferred embodiment, however, the method of the invention is applied to lipases. The method of invention may be applied to any mixture containing a lipolytic enzyme.

By the method of the invention, lipase containing mixtures comprising the desired lipase in concentrations as low as 1% (w/w) may successfully be subjected to enzyme separation by crystallization. In addition, lipase containing mixtures comprising other proteins (including other enzymes) in concentrations of more than 50% (w/w), preferably below 50% (w/w), of the total protein content may successfully be subjected to enzyme separation by crystallization.

The lipolytic enzyme may be of fungal or bacterial origin. In a preferred embodiment, the process is applied to glycolipases. In another preferred embodiment, the process is applied to acidic lipases, i.e. lipases with a pI value in the range of from 3 to 7, more preferred in the range of from 3.5 to 5.5.

Examples of lipases of fungal origin suited for the process of invention are lipases obtainable from members of the genera Aspergillus (e.g. *A. niger*); Candida (e.g. *C. antarctica*); Humicola (e.g. *H. lanuginosa* and *H. insolens*); and Rhizomucor (e.g. *R. miehei*).

Examples of lipases of bacterial origin suited for the process of the invention are lipases obtainable from members of the genus Pseudomonas (e.g. *Ps. cepacia*).

Lipase containing solutions can be obtained by fermentation of a lipase producing microorganism. In most cases, however, the lipase producing organism will be a host organism carrying an inserted gene encoding the desired lipase, e.g. a Humicola lipase or a Rhizomucor lipase, expressed in *Aspergillus oryzae* (vide EP Publication Nos. 238,023 and 305,216).

In a preferred embodiment, the method is applied to separation of a lipase, the lipases being either intracellular or extracellular, from a culture broth. After cultivation cell lysis may be accomplished, and the culture broth subjected to solid/liquid separation by centrifugation.

By the method of invention salts and other low molecular weight impurities are leached out from the aqueous solution, thereby obtaining a low ionic strength of the solution. These low molecular substances may be removed by diafiltration, dialysation, or electrodialysation, or by gelfiltration, or by chromatographic methods, or by precipitation. Diafiltration, dialysation, or electrodialysation is preferred, using a membrane with a cut-off value below the molecular weight of the lipase in question.

The ionic strength of the solution may conveniently be monitored with a conductivity meter. In the context of this invention, low ionic strength is represented by a conductance of 10 mS/cm or less, preferably 5 mS/cm or less, most preferred 2 mS/cm or less.

Subsequent to removal of the low molecular impurities the pH of the aqueous solution is adjusted to a pH value in the range of ±3 around the pI of the lipase, more preferred in the range of ±1.5 around the pI of the lipase, yet more preferred in the range of ±1 around the pI of the lipase, most preferred in the range of 0.5 around the pI of the lipase.

The pH of the aqueous solution may be adjusted by use of virtually any acid or base. The acid may be organic or inorganic. Some examples are hydrochloric acid, sulfuric acid, nitrous acid, phosphoric acid, acetic acid, citric acid, and formic acid. Preferred acids are formic acid, citric acid, or acetic acid.

The method of invention may be applied to aqueous lipase containing solutions having a lipase content as low as 1% (w/w). Preferably the method of invention is applied to aqueous lipase containing solutions having a lipase content of more than 5% (w/w), in particular 5–20% (w/w), more preferred 10–20% (w/w), and a lipase content higher than 10% of total DS (dry substance), preferably a lipase content higher than 30% of total DS.

In a more specific embodiment of this invention, a preliminary precipitation of the ultrafiltrate concentrate by conventional means may be carried out, e.g. with sodium or ammonium sulfate, followed by redissolution of the filter cake, and ultrafiltration of the redissolved lipase, and optionally removal of salts by diafiltration and/or dilution.

If crystalline products of very high purity are desirable, e.g. lipases for therapeutical applications, the process of the invention may be repeated, i.e. the crystalline end product of the process of the invention is redissolved and subjected to one or more additional crystallization processes.

The following examples further illustrate the present invention, and they are not intended to be in any way limiting to the scope of the invention as claimed.

EXAMPLE 1

This example demonstrates the method of the invention applied to separation of a *Humicola lanuginosa* lipase from a culture broth, obtained as described in EP publication No. 305,216.

The culture broth was subjected to centrifugation and ultrafiltration/diafiltration using membrane with a cut-off value of 20 kD, and was diafiltrated to a conductance of 3 mS/cm. The diafiltrate contained 13% of lipase (w/w) and 20% of total dry substance (w/w), which means that 65% of the total dry substance was lipase. pH was adjusted to 4.5 with citric acid.

Table 1 presents the result of this example in comparison to a conventional crystallization process involving addition of salts. The table expresses % of yield and purity measured.

The purity is expressed in lipase activity. One Lipase Unit (LU; 1000 LU=1 KLU) is the amount of enzyme which liberates 1 µmole titratable butyric acid per minute at 30.0° C.; pH 7.0, with Gum Arabic as emulsifier and tributyrin as substrate.

TABLE 1

| Additions | Crystallization time | | Purity | |
| --- | --- | --- | --- | --- |
| | 15 h (25° C.) | 15 h (25° C.) + 48 h (5° C.) | KLU/$A_{280}$ | KLU/$A_{440}$ |
| None | 90% | — | 3.8 | 805 |
| 1% $Na_2SO_4$ [1 | 14% | 85% | 3.2 | 680 |
| 3% $Na_2SO_4$ [2 | 12% | 79% | 3.2 | 650 |
| 3% Na-formate [3 | 8% | 71% | 3.1 | 660 |

[1 1% $Na_2SO_4$ = 13 mS/cm
[2 3% $Na_2SO_4$ = 31 mS/cm
[3 3% Na-formate = 15 mS/cm This example demonstrates the surprising effects of the process according to the invention: High yield, high purity, and short time of crystallization.

EXAMPLE 2

This example demonstrates the method of the invention applied to separation of a *Humicola lanuginosa* lipase from a culture broth, obtained as described in EP publication No. 305,216.

The culture broth was subjected to centrifugation and ultrafiltration/diafiltration using membrane with a cut-off value of 20 kD, and was diafiltrated to a conductance of 3 mS/cm. The diafiltrate contained 11% of lipase (w/w) and 20% of total dry substance (w/w). pH was adjusted to 4.3 with citric acid.

Table 2 presents the result of this example in comparison to a conventional crystallization process involving addition of salts. The table expresses % of yield.

TABLE 2

| Additions | Crystallization time 21 h (25° C.) |
| --- | --- |
| None | 80% |
| 8% $(NH_4)_2SO_4$ [1 | 40% |

TABLE 2-continued

| Additions | Crystallization time 21 h (25° C.) |
|---|---|
| 12% (NH$_4$)$_2$SO$_4$ (2 | 40% |
| 18% (NH$_4$)$_2$SO$_4$ (3 | 32% |
| 9% Na$_2$SO$_4$ (4 | 43% |

(1 8% (NH$_4$)$_2$SO$_4$ = 92 mS/cm
(2 12% (NH$_4$)$_2$SO$_4$ = 126 mS/cm
(3 18% (NH$_4$)$_2$SO$_4$ = 165 mS/cm
(4 9% Na$_2$SO$_4$ = 71 mS/cm

This example demonstrates the high yield of the process of the invention.

EXAMPLE 3

This example demonstrates the method of the invention applied to separation of a *Rhizomucor miehei* lipase from a culture broth, obtained as described in EP publication No. 238,023.

The culture broth was subjected to centrifugation and ultrafiltration/diafiltration using membrane with a cut-off value of 20 kD, and was diafiltrated to a conductance of 2.5 mS/cm. The diafiltrate contained 10% of lipase (w/w) and 16% of total dry substance (w/w). pH was adjusted to 5.0 with citric acid.

Table 3 presents the result of this example in comparison to a conventional crystallization process involving addition of salts. The table expresses % of yield.

TABLE 3

| | Crystallization time | | | |
|---|---|---|---|---|
| Additions | 2 h (25° C.) | 4 h (25° C.) | 4 h (25° C.) + 21 h (5° C.) | 4 h (25° C.) + 96 h (5° C.) |
| None | 70% | 70% | 70% | 70% |
| 2% (NH$_4$)$_2$SO$_4$ (1 | — | 35% | 70% | 70% |
| 4% (NH$_4$)$_2$SO$_4$ (2 | — | 11% | 45% | 68% |
| 7% (NH$_4$)$_2$SO$_4$ (3 | — | 3% | 6% | 20% |
| 10% (NH$_4$)$_2$SO$_4$ (4 | — | — | <3% | 5% |

(1 2% (NH$_4$)$_2$SO$_4$ = 28 mS/cm
(2 4% (NH$_4$)$_2$SO$_4$ = 54 mS/cm
(3 7% (NH$_4$)$_2$SO$_4$ = 83 mS/cm
(4 10% (NH$_4$)$_2$SO$_4$ = 108 mS/cm

This example demonstrates the high yield and the short crystallization time of the process of the invention.

EXAMPLE 4

This example demonstrates the method of the invention applied to a *Humicola lanuginosa* lipase, obtained as described in EP publication No. 305,216.

Five experiments were carried out. The above culture broth was subjected to centrifugation and ultrafiltration using membrane with a cut-off value of 20 kD, and was diafiltrated to a conductance of 1 mS/cm. The diafiltrate contained 18% of dry substance in total. pH was adjusted to pH 4.3 with formic acid. The solution was stirred for 20 hours at 28° C. The results are presented in Table 4 below.

TABLE 4

| % lipase (w/w) | % other enzymes (w/w) | % total DS (w/w) | % crys. yield* |
|---|---|---|---|
| 9.4 | 3.2 | 18 | 72 |
| 8.6 | 3.8 | 18 | 71 |
| 8.3 | 4.3 | 18 | 68 |
| 7.4 | 4.8 | 18 | 63 |
| 7.1 | 5.3 | 18 | 61 |

*) crystallization yield

This example demonstrates that excellent yields are obtained by the method of the invention even if the method is applied to low concentrations of the lipase, and even if other enzymes are present in relatively high concentrations.

We claim:

1. A method for obtaining an enzyme of interest in a crystalline form from a solution of mixed proteins, said method comprising (a) forming a low ionic strength solution from said solution, wherein said low ionic strength solution has a conductance of up to 10 mS/cm;

(c) adjusting the pH of the low ionic strength solution of step (a) to about the pI of the enzyme of interest, wherein said enzyme crystallizes; and (d) recovering the enzyme of interest in crystalline form.

2. The method of claim 1, wherein said low ionic strength solution is formed by removing salts present in said solution by diafiltration, dialysation, electrodialysation, gel filtration, chromatography, or precipitation.

3. The method of claim 1, wherein said low ionic strength solution has a conductance of up to 5 mS/cm.

4. The method of claim 3, wherein said low ionic strength solution has a conductance of up to 2 mS/cm.

5. The method of claim 1, wherein said pH is adjusted to a pH value in the range of ±3 pH units around the pI of the enzyme.

6. The method of claim 1, wherein said pH is adjusted to a pH value in the range of ±1.5 pH units around the pI of the enzyme.

7. The method of claim 1, wherein said pH is adjusted to a pH value in the range of ±0.5 pH units around the pI of the enzyme.

8. The method of claim 1, wherein said enzyme of interest is a lipase.

9. The method of claim 8, wherein said lipase is present in a concentration range of between 1–20% (w/w) in said solution.

10. The method of claim 8, wherein said lipase comprises more than 10% of the total dry substance of said solution.

11. The method of claim 8, wherein said lipase is a fungal or bacterial lipase.

12. The method of claim 11, wherein said fungal lipase is isolated from a strain from the genus Aspergillus, Candida, Humicola, or Rhizomucor.

13. The method of claim 11, wherein said bacterial lipase is isolated from a strain from the genus Pseudomonas.

* * * * *